(12) United States Patent
Herweg et al.

(10) Patent No.: US 11,933,751 B2
(45) Date of Patent: Mar. 19, 2024

(54) METHOD FOR ASSESSING THE OPERATABILITY OF A SENSOR FOR DETECTING SOOT

(71) Applicant: Robert Bosch GmbH, Stuttgart (DE)

(72) Inventors: Karola Herweg, Stuttgart (DE); Carolin Maria Schilling, Bad Schoenborn (DE); Mathias Klenk, Loechgau (DE)

(73) Assignee: ROBERT BOSCH GMBH, Stuttgart (DE)

( * ) Notice: Subject to any disclaimer, the term of this patent is extended or adjusted under 35 U.S.C. 154(b) by 171 days.

(21) Appl. No.: 17/292,369

(22) PCT Filed: Sep. 16, 2019

(86) PCT No.: PCT/EP2019/074619
§ 371 (c)(1),
(2) Date: May 7, 2021

(87) PCT Pub. No.: WO2020/098995
PCT Pub. Date: May 22, 2020

(65) Prior Publication Data
US 2022/0003705 A1    Jan. 6, 2022

(30) Foreign Application Priority Data

Nov. 16, 2018 (DE) .......................... 102018219625.7

(51) Int. Cl.
*G01N 27/04* (2006.01)
(52) U.S. Cl.
CPC ......... *G01N 27/045* (2013.01); *G01N 27/043* (2013.01)
(58) Field of Classification Search
CPC .......................... G01N 27/045; G01N 27/043
See application file for complete search history.

(56) References Cited

U.S. PATENT DOCUMENTS

| 2011/0030451 A1 | 2/2011 | Roesch et al. |
| 2011/0088450 A1* | 4/2011 | Ante ...................... F02D 41/222 |
| | | 73/23.33 |

(Continued)

FOREIGN PATENT DOCUMENTS

| CN | 105386836 A | 3/2016 |
| DE | 102012210525 A1 | 12/2013 |

(Continued)

OTHER PUBLICATIONS

International Search Report for PCT/EP2019/074619, dated Jan. 7, 2020.

*Primary Examiner* — Feba Pothen
(74) *Attorney, Agent, or Firm* — NORTON ROSE FULBRIGHT US LLP; Gerard A. Messina

(57) ABSTRACT

A method for evaluating the functionality of a ceramic sensor for detecting soot, the sensor including two measurement electrodes exposable to an exhaust and spaced apart from one another, and an electrical resistance heating element. The method includes: activating the resistance heating element to heat up the sensor and to burn soot off the two measurement electrodes; then deactivating the resistance heating element; then waiting for a first predetermined time period and/or waiting until a signal that is received from the sensor and represents the sensor temperature reaches a first predefined value; then measuring a first variable representing the electrical resistance between the measurement electrodes; then evaluating the functionality of the sensor based on the first variable representing the electrical resistance between the measurement electrodes.

8 Claims, 3 Drawing Sheets

(56) References Cited

U.S. PATENT DOCUMENTS

| | | | |
|---|---|---|---|
| 2011/0314899 A1 | 12/2011 | Di Miro et al. | |
| 2015/0177204 A1* | 6/2015 | Bessen | G01M 15/102 |
| | | | 73/114.71 |
| 2016/0356693 A1* | 12/2016 | Tylutki | F01N 11/002 |

FOREIGN PATENT DOCUMENTS

| | | |
|---|---|---|
| DE | 102014220398 A1 | 4/2016 |
| EP | 1630369 A2 | 3/2006 |
| WO | 2003006976 A2 | 1/2003 |

* cited by examiner

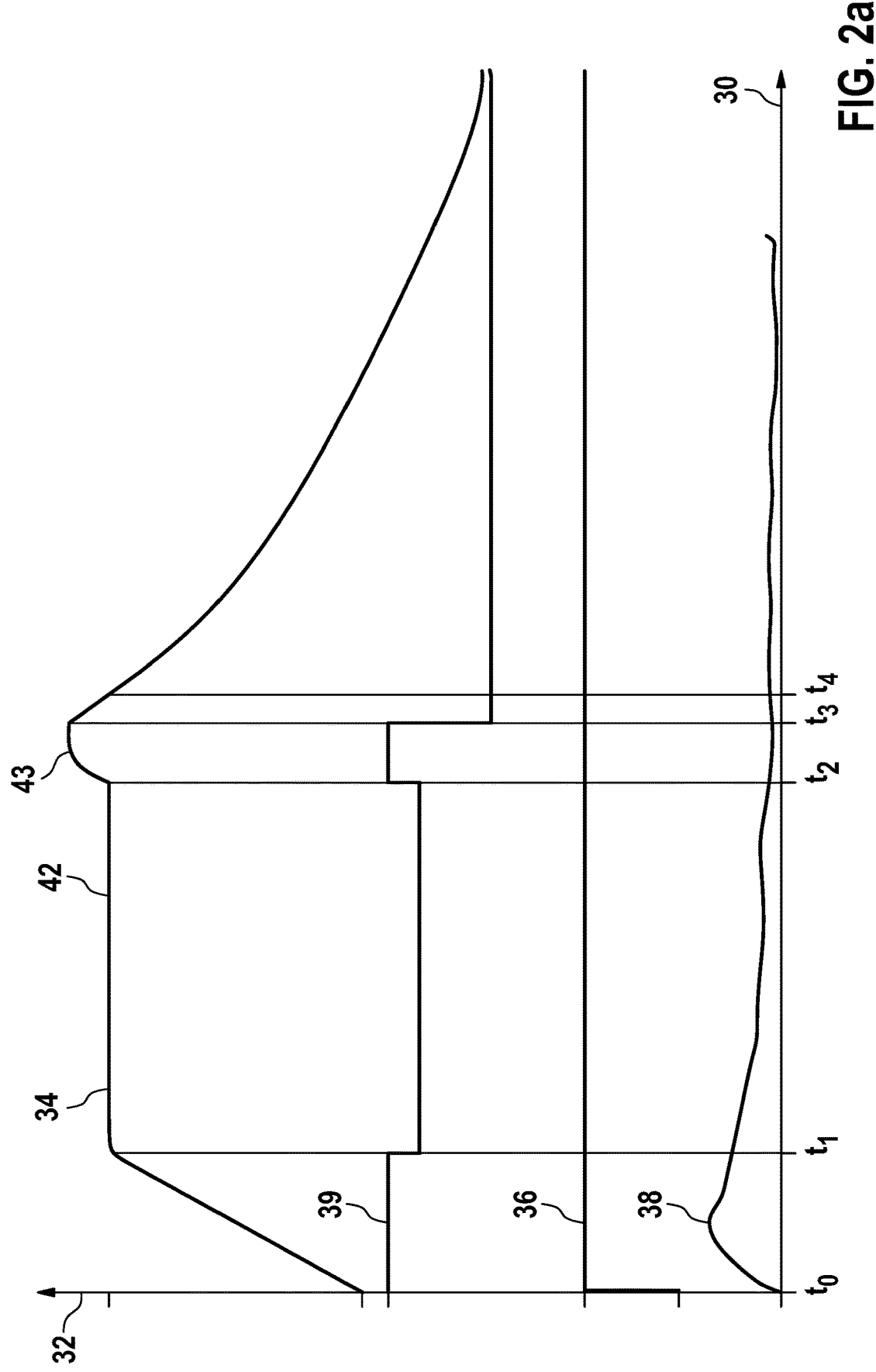

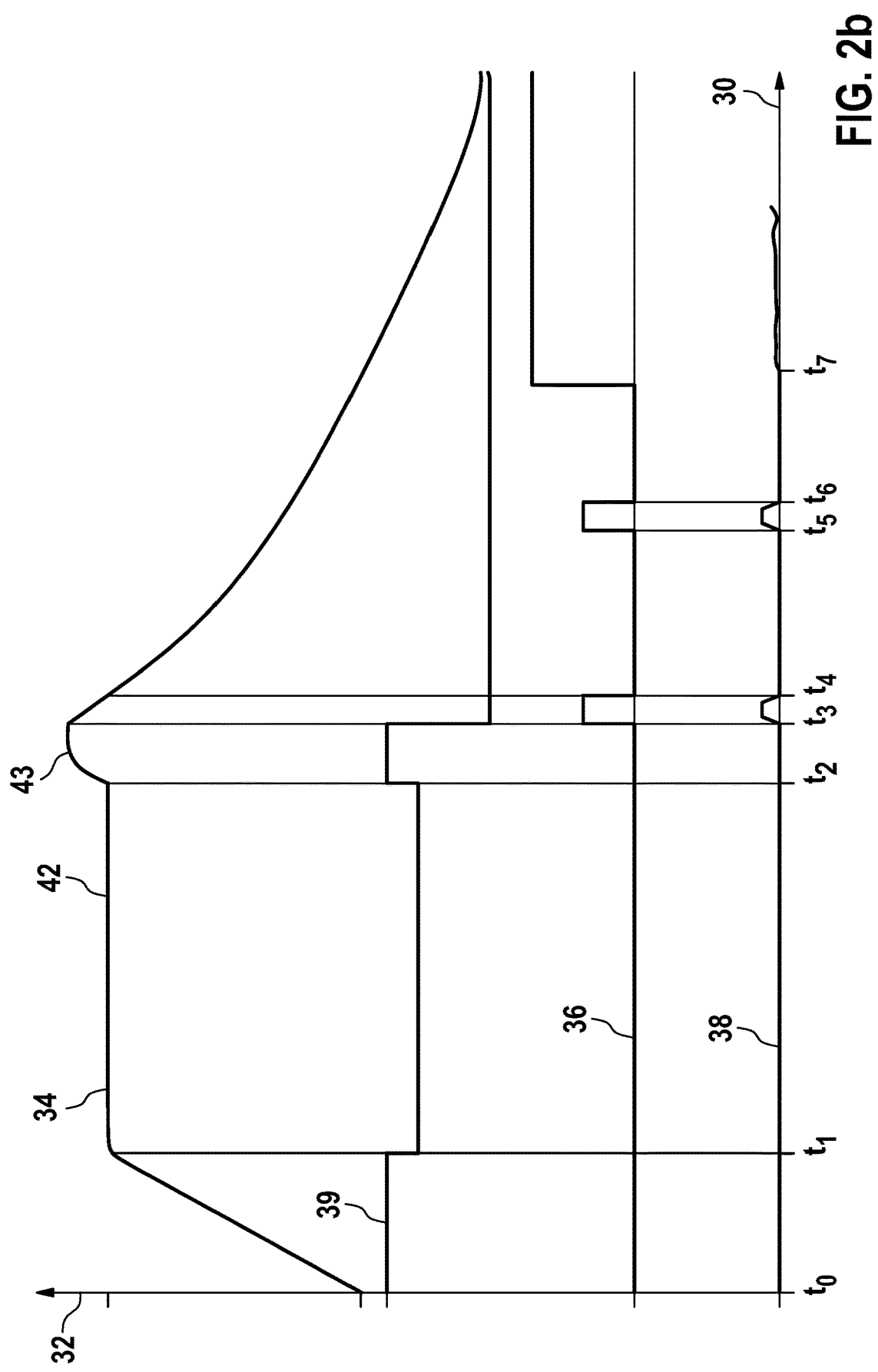

METHOD FOR ASSESSING THE OPERATABILITY OF A SENSOR FOR DETECTING SOOT

BACKGROUND INFORMATION

German Patent Application No. DE 10 2012 210 525 A1 describes a method and an apparatus for detecting soot particles in the exhaust gas of internal combustion engines.

Ceramic resistive soot sensors, having two measurement electrodes exposable to an exhaust gas and a resistance heating element, are conventional. Measurement of a soot concentration in the exhaust gas is based on deposition of the soot particles between the measurement electrodes and a consequently reduced electrical resistance between the measurement electrodes. The soot particles can be burned off using the resistance heating element, so that a new measurement can be started.

It is also conventional to monitor the integrity of the electrodes, and thus the functionality of the sensor, by the fact that after a regeneration, i.e., when a conductive connection due to soot is ruled out, the temperature of the sensor is held constant with a resistance heating element and at the same time a voltage is applied to the electrode; the electrodes are evaluated as intact if a resulting measured current is above a threshold value. A measurement method that provides for two measurements of the resulting measured currents at two different sensor temperatures is also described in German Patent Application No. DE 10 2012 210 525 A1.

SUMMARY

The present invention is based on the inventors' recognition that the measurement of a current between the measurement electrodes of the ceramic sensor for the purpose of evaluating the functionality of a sensor can potentially be distorted by heating of the sensor during the measurement. It has been recognized in particular that the voltages or potentials applied to the electrical resistance heating element are capable of displacing ions in the sensor, thus resulting in electrical currents to the measurement electrodes or between the measurement electrodes or to a control device connected to the measurement electrodes, which currents distort the actually intended measurement of the measured current correlated with the measurement voltage applied between the measurement electrodes. It has also been recognized, in particular, that switching-on and shut-off operations of the resistance heating element, which are associated, for example, with regulation of the sensor temperature to a constant temperature, result in disruptions to the measured current.

Provision is therefore made according to an example embodiment of the present invention to deactivate the resistance heating element after soot has been burned off the measurement electrodes, so that the electrical heating output during the subsequent steps of the method according to the present invention is equal to 0 W, and it no longer causes any movement of ions in the sensor. After a delay, the resistance heating element is deactivated, a measurement of a first variable representing the electrical resistance between the measurement electrodes can then be carried out with high accuracy. The evaluation of the functionality of the sensor can consequently also be carried out with increased reliability.

In the context of the present disclosure, "electrical resistances" are considered to be variables that are produced by dividing a voltage by a current, i.e., having, for example, the unit of ohms.

In the context of the present disclosure, variables that represent an electrical resistance are also understood to be variables that, at least in the present context, unequivocally correlate with an electrical resistance. For example, the variable representing the electrical resistance can be the electrical resistance; or, in the context of a given voltage, the variable representing the electrical resistance can be a current or an inverse current. In another example, in the context of a given current the variable representing the electrical resistance can be a voltage.

The delay can be a predefined waiting time, for example a waiting time of at least 50 ms and/or a waiting time of at most one second.

The delay can, however, also involve waiting until the sensor has cooled to a predefined temperature and until a signal that is received from the sensor and represents the sensor temperature reaches a corresponding first predefined value. That temperature can be, for example, 780° C. or a value between 700° C. and 800° C.

The signal representing the sensor temperature can be, for example, a signal representing an electrical resistance (see above). The sensor can have, for example, a temperature measuring element, for instance a Pt100 or the like, and can have control correspondingly applied to it by the method according to the present invention.

According to a refinement of the present invention, provision is made that after the measurement of the first variable representing the electrical resistance between the measurement electrodes, a second delay is observed and then a second variable representing the electrical resistance between the measurement electrodes is measured, and the functionality of the sensor is then evaluated based on the first variable representing the electrical resistance between the measurement electrodes and based on the second variable representing the electrical resistance between the measurement electrodes. Offset effects can thereby be eliminated, and the reliability of the evaluation of the functionality of the sensor can be further improved. For example, the second variable representing the electrical resistance between the measurement electrodes can be subtracted from the first variable representing the electrical resistance between the measurement electrodes, and the functionality of the sensor can be evaluated on the basis of the resulting difference.

The fact that the temperature of the sensor generally decreases after deactivation of the resistance heating element can be compensated for by the fact that the sensor is firstly heated to an overtemperature. For example, in order to burn soot off the two measurement electrodes the sensor can be heated to a first predefined temperature that is held for at least 5 s and is in the range between 700° C. and 850° C.; and before the resistance heating element is deactivated the sensor can be heated further with the resistance heating element to a predefined overtemperature that is at least 10 K higher than the first predefined temperature, i.e., for example between 710° C. and 860° C. Provision can be made that the overtemperature is no more than 40 K higher than the first predefined temperature.

The inventors have furthermore recognized that transient effects can occur in the context of measurement of the first variable representing the electrical resistance between the measurement electrodes, and can in turn result in measurement inaccuracies. It has been observed, for example, that directly after the measurement voltage between the measurement electrodes is applied or increased, particularly high currents result for a short time due to the movement of ions in the sensor.

Refinements of the present invention may avoid these effects and thus increase the reliability of the evaluation of the functionality of the sensor. They provide that already during activation of the resistance heating element in order to heat up the sensor and burn soot off the two measurement electrodes, a voltage is applied between the measurement electrodes. This voltage is then maintained in constant and uninterrupted fashion during the subsequent method steps, i.e., in particular during deactivation of the resistance heating element, during the delay until a signal that is received from the sensor and represents the sensor temperature reaches a first predefined value, during measurement of a first variable representing the electrical resistance between the measurement electrodes, and if applicable during further method steps that precede evaluation of the functionality of the sensor.

In experiments by the Applicant it has proven to be favorable if this applied voltage is relatively high, i.e., for example is equal to more than 12 V. It can also, for example, be equal to more than 40 V.

The present invention also encompasses: a computer program that is configured to carry out the steps of the method according to the present invention; a nonvolatile memory on which such a computer program is stored; and an electronic control unit that encompasses such a nonvolatile memory.

BRIEF DESCRIPTION OF THE DRAWINGS

FIGS. 2a and 2b are time diagrams of the method according to an example embodiment of the present invention.

DETAILED DESCRIPTION OF EXAMPLE EMBODIMENTS

Figure 1:
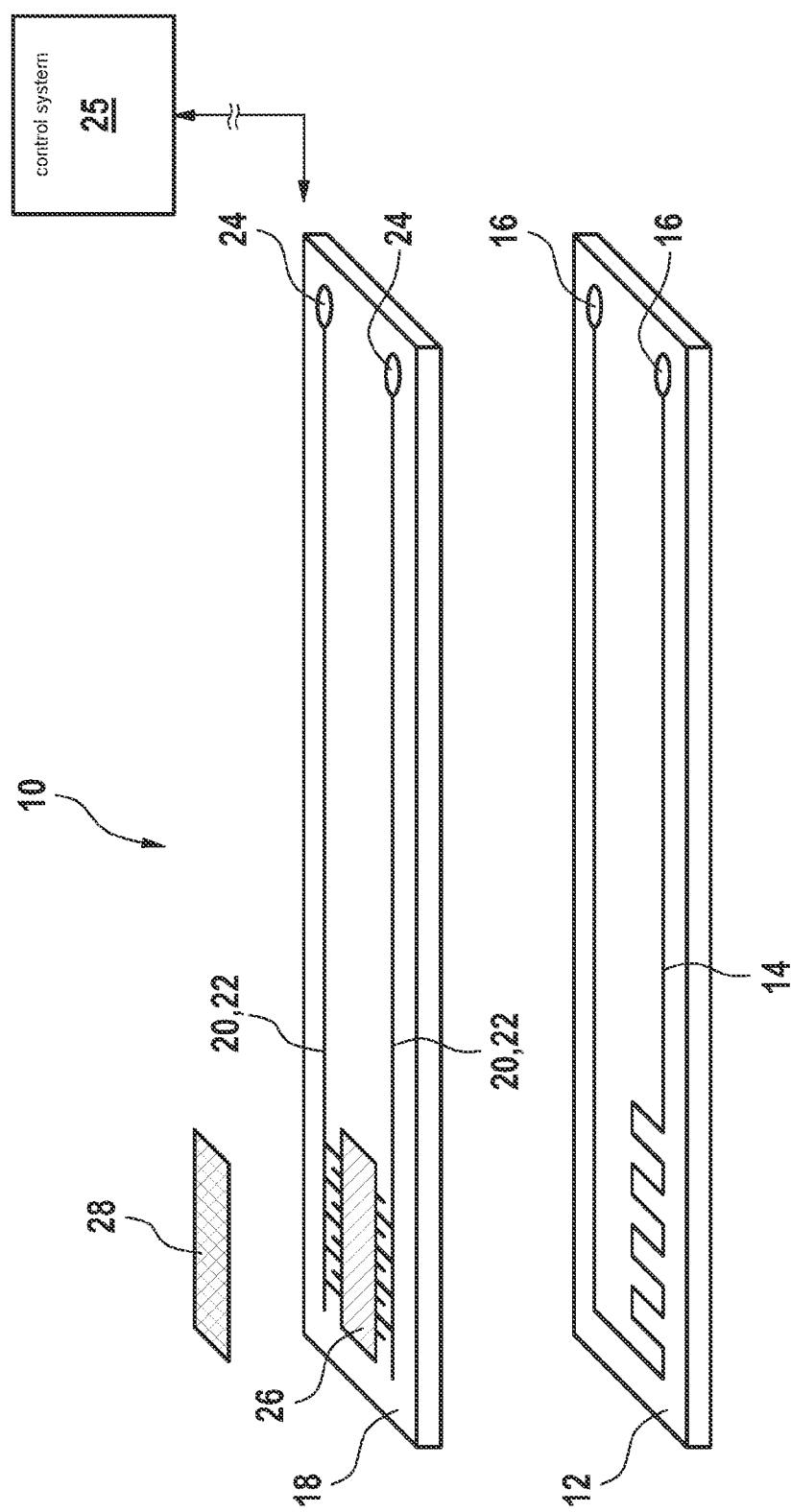
FIG. 1 shows a ceramic sensor for detecting soot.

FIG. 1 shows a sensor 10 for detecting soot in a gas flow, for example in an exhaust gas flow of an internal combustion engine, which serves for installation in an exhaust system of a motor vehicle. Sensor 10 is disposed, for example, downstream from a soot filter of a motor vehicle having a diesel internal combustion engine.

Sensor 10 encompasses a plate-shaped carrier layer 12 that is produced at least in part from an electrically insulating material, for example from a ceramic such as aluminum oxide. Integrated into carrier layer 12 is a resistance heating element 14 that is connectable via contacts 16 to a suitable voltage source and serves to burn off from sensor 10 particles, such as soot particles, that may have been deposited.

Arranged on carrier layer 12 is a plate-shaped substrate 18 that is produced at least in part from an electrically insulating material, for example a ceramic such as aluminum oxide. A structure made up of two measurement electrodes 20 is disposed on substrate 18. Measurement electrodes 20 are embodied, for example, as interdigital electrodes 22 so that they engage in comb fashion into one another. Measurement electrodes 20 are connectable via contacts 24 to a control system 25.

In the region in which measurement electrodes 20 engage in comb fashion into one another, measurement electrodes 20 can be covered at least in part by a dielectric 26, so that measurement electrodes 20 can serve as electrodes of a capacitor having a measurable capacitance. Dielectric 26 can in turn be equipped with a protective layer 28 so that it is isolated with respect to the surrounding medium, thereby precluding degeneration of dielectric 26.

Sensor 10 can furthermore encompass a housing that surrounds the configuration depicted in FIG. 1 and is not shown in FIG. 1.

The sensor in accordance with FIG. 1 can operate as follows: When soot or other electrically conductive particles become deposited on substrate 18, this reduces an electrical resistance between the two measurement electrodes 20. A measurement of the impedance between the two measurement electrodes 20 produces a behavior that is typical of an RC element. This means that the concentration of soot or particles in the relevant exhaust gas can be determined based on the change over time in the resistance component of the RC element.

In order to regenerate sensor 10, after a certain time the deposited particles are burned off by way of resistance heating element 14 integrated into carrier layer 12. When sensor 10 is functioning correctly, after this heating the resistance between measurement electrodes 20 should rise considerably and should be defined by the conductivity of the layers of sensor 10 which surround measurement electrodes 20. Because the manner of operation of sensor 10 for detecting the particle concentration is conventional, for example, as described in PCT Patent Application No. WO 2003/006976 A2, so the usual operation of sensor 10 will not be discussed in further detail at this juncture, and the content of the aforementioned related art as it relates to describing the manner of operation of sensor 10 is entirely incorporated herein by reference. Instead, the method according to the present invention for monitoring the function of sensor 10 will now be described. The method can be carried out, for example, by the aforementioned control system 25. The method is described in particular with reference to FIGS. 2a and 2b.

In particular, in FIG. 2a time is depicted on X axis 30, and the change over time in specific variables, such as a temperature 34, an electrical voltage 36 existing between measurement electrodes 20, and an electrical current 38 flowing between measurement electrodes 20, as well as a heating output 39 of resistance heating element 14, is plotted on Y axis 32.

FIG. 2a shows, for example, the above-described burnoff or heating of sensor 10. For this, sensor 10 is heated by way of resistance heating element 14, as is evident, e.g., from the curve for temperature 34 starting from first time to. Sensor 10 is heated until a first predefined temperature 42 is reached at time t1. From time t1 to time t2, first temperature 42 is held constant, for example, over a time span of 45 s, and is equal, for example, to 785° C. Because the temperature is not increased further between times t1 and t2, the heating output is less during this time than between times t0 and t1.

Between times t2 and t3 the heating output is elevated again, for example to the same value as between times t0 and t1. The temperature consequently rises to an overtemperature 43, for example to 805° C., at time t3.

At time t3, electrical resistance heating element 14 is deactivated, i.e., thereafter, and within the remaining measurement cycle or during the further steps of the method for evaluating the functionality of the sensor, electrical heating output 39 is always equal to a value of 0 W. Because of the thermal coupling of sensor 10 to its environment, it cools off. For example, 650 ms later, at time t4, it again reaches a temperature of 785° C.

Provision is made that now, at time t4, the measurement of a first variable representing the electrical resistance between measurement electrodes 20, for example the measurement of electrical current 38 flowing between measurement electrodes 20, is performed.

Also depicted in FIG. 2a is the profile of electrical voltage 36 applied between measurement electrodes 20. In this example, this voltage is a constant 45.6 V from time t0 until after time t4.

From the measured electrical current 38 flowing between measurement electrodes 20 and the known electrical voltage 36 applied between measurement electrodes 20, the electrical resistance between measurement electrodes 20 can be inferred.

If this resistance is lower than a predefined threshold value, the sensor is evaluated as functional. If this resistance is higher than the predefined threshold value, however, the sensor is evaluated as nonfunctional. For example, a corresponding entry can be made in a fault memory register, or an engine control light (malfunction indicator light, MIL) can be activated in order to indicate a fault.

Sensor 10 cools off further after time t4, and below a specific temperature soot can once again become deposited on measurement electrodes 20. The next measurement cycle has thus already begun.

A modified exemplifying embodiment of the present invention is depicted in FIG. 2b. It differs from the above-explained exemplifying embodiment firstly in that measurement voltage 36 present between measurement electrodes 20 has a value of 0 V between times t0 and t3, and has a value of 7.5 V between times t3 and t4. This value is used in order to determine the first electrical resistance. At time t7, at which the next measurement cycle begins, measurement voltage 36 present between measurement electrodes 20 is switched to a value of 45.6 V.

The exemplifying embodiment of the present invention depicted in FIG. 2b differs further from the example explained earlier in that at a time t5, at a fixed time after time t4, or when sensor 10 reaches a second temperature, a second variable representing the electrical resistance between measurement electrodes 20 is determined. For this, similarly to between times t3 and t4, measurement voltage 36 existing between measurement electrodes 20 is switched to a value of 7.5 V until time t6. The functionality of sensor 10 is evaluated based on the first resistance and the second resistance, for example based on the difference between those values.

What is claimed is:

1. A method for evaluating a functionality of a ceramic sensor for detecting soot, the sensor including two measurement electrodes exposable to an exhaust and spaced apart from one another, and an electrical resistance heating element, the method comprising the following steps:
activating the resistance heating element to heat up the sensor and to burn soot off the two measurement electrodes;
after the activating step, deactivating the resistance heating element;
after the deactivating step, waiting for a first predetermined time period and/or waiting until a signal that is received from the sensor represents that a sensor temperature reaches a first predefined value;
after the waiting step, measuring a first variable representing an electrical resistance between the measurement electrodes; and
after the measuring step, evaluating the functionality of the sensor based on the first variable representing the electrical resistance between the measurement electrodes,
wherein before the resistance heating element is deactivated, the sensor is heated further with the resistance heating element to a predefined overtemperature that is at least 10 K higher than a first predefined temperature.

2. The method as recited in claim 1, further comprising:
after the measuring of the first variable representing the electrical resistance between the measurement electrodes:
waiting for a second predetermined time period or waiting until a signal that is received from the sensor represents the sensor temperature reaches a second predefined value, and
measuring a second variable representing the electrical resistance between the measurement electrodes;
wherein the functionality of the sensor is evaluated in the evaluating step based on the first variable representing the electrical resistance between the measurement electrodes and based on the second variable representing the electrical resistance between the measurement electrodes.

3. The method as recited in claim 1, wherein to burn soot off the two measurement electrodes, the sensor is heated to the first predefined temperature that is held for at least 5 s and is in a range between 700° C. and 850° C.

4. The method as recited in claim 1, wherein during the activation of the resistance heating element, to heat up the sensor and burn soot off the two measurement electrodes, a voltage is applied between the measurement electrodes.

5. The method as recited in claim 4, wherein the voltage applied between the measurement electrodes during the activation of the resistance heating element to heat up the sensor and burn soot off the two measurement electrodes is maintained in subsequent method steps.

6. The method as recited in claim 4, wherein the voltage applied between the measurement electrodes during the activation of the resistance heating element to heat up the sensor and burn soot off the two measurement electrodes is equal to more than 12 V.

7. A nonvolatile memory on which is stored a computer program for evaluating a functionality of a ceramic sensor for detecting soot, the sensor including two measurement electrodes exposable to an exhaust and spaced apart from one another, and an electrical resistance heating element, the computer program, when executed by a computer, causing the computer to perform the following steps:
activating the resistance heating element to heat up the sensor and to burn soot off the two measurement electrodes;
after the activating step, deactivating the resistance heating element;
after the deactivating step, waiting for a first predetermined time period and/or waiting until a signal that is received from the sensor represents that a sensor temperature reaches a first predefined value;
after the waiting step, measuring a first variable representing an electrical resistance between the measurement electrodes; and
after the measuring step, evaluating the functionality of the sensor based on the first variable representing the electrical resistance between the measurement electrodes,
wherein before the resistance heating element is deactivated, the sensor is heated further with the resistance heating element to a predefined overtemperature that is at least 10 K higher than a first predefined temperature.

8. An electronic control unit configured to evaluate a functionality of a ceramic sensor for detecting soot, the sensor including two measurement electrodes exposable to an exhaust and spaced apart from one another, and an electrical resistance heating element, the electronic control unit configured to:
- activate the resistance heating element to heat up the sensor and to burn soot off the two measurement electrodes;
- after the activation, deactivate the resistance heating element;
- after the deactivation, wait for a first predetermined time period and/or wait until a signal that is received from the sensor represents that a sensor temperature reaches a first predefined value;
- after the wait, measure a first variable representing an electrical resistance between the measurement electrodes; and after the measurement, evaluate the functionality of the sensor based on the first variable representing the electrical resistance between the measurement electrodes,
- wherein before the resistance heating element is deactivated, the sensor is heated further with the resistance heating element to a predefined overtemperature that is at least 10 K higher than a first predefined temperature.

* * * * *